United States Patent [19]
Montgomery

[11] Patent Number: 5,197,465
[45] Date of Patent: Mar. 30, 1993

[54] GAUGE FOR MEASURING TRACHEOTOMY STOMA

[75] Inventor: Stuart K. Montgomery, Needham, Mass.

[73] Assignee: Boston Medical Products, Inc., Waltham, Mass.

[21] Appl. No.: 809,728

[22] Filed: Dec. 17, 1991

[51] Int. Cl.⁵ .............................................. A61M 16/04
[52] U.S. Cl. ............................ 128/207.29; 33/501.45; 33/512; 128/200.26
[58] Field of Search .......... 128/67, 341, 25 R, 200.26, 128/207.14, 207.15, 207.16, 207.29, 778; 604/21, 93, 100, 117, 264; 606/102, 103, 108; 33/511, 512, 529, 542, 544.5, 544.6, 545, 836, 501.45; 7/164, 169; 433/75

[56] References Cited

U.S. PATENT DOCUMENTS

| | | | |
|---|---|---|---|
| 930,330 | 8/1909 | Coe | 33/542 |
| 2,582,679 | 1/1952 | Carroll | 33/501.45 |
| 2,715,281 | 8/1955 | Black | 33/501.45 |
| 3,105,401 | 10/1953 | Diamond | 33/501.45 |
| 3,740,779 | 6/1973 | Rubricuis | 128/25 R X |
| 4,240,412 | 12/1980 | James | 128/67 |
| 4,269,184 | 5/1981 | Montgomery | 128/207.14 |
| 4,362,167 | 12/1982 | Nicolai et al. | 33/512 |
| 4,483,075 | 11/1984 | Kundin | 33/512 |
| 4,972,845 | 11/1990 | Iversen et al. | 128/780 |
| 5,013,318 | 5/1991 | Spranza, III | 33/512 X |
| 5,042,161 | 8/1991 | Hodge | 33/501.45 |

Primary Examiner—V. Millin
Assistant Examiner—William M. Pierce
Attorney, Agent, or Firm—Fish & Richardson

[57] ABSTRACT

A tool for measuring a tracheotomy stoma for proper fitting of a tracheotomy tube including an integral member having a plurality of legs and a shaft that extend from it, each leg having a free end and a base end secured to other legs, each leg being sufficiently long to extend from the outside of a patient's skin to inside the tracheal passage, each leg being spaced from other legs by at least about 90° or more so as to not interfere with insertion into the tracheotomy stoma, each leg being generally cylindrical over most of its length and having a diameter that corresponds to a tracheal tube diameter and is different than the diameter of other legs, the shaft having a bent end for engaging the inside surface of the tracheal passage and length indicia along its length indicating the distance to the bent end, and a ring sized and shaped to releasably engage the shaft at various positions along said shaft so as to indicate a particular length indicia when pushed up against the patient's skin when the bent end engages the inside surface of a tracheal passage.

16 Claims, 1 Drawing Sheet

GAUGE FOR MEASURING TRACHEOTOMY STOMA

BACKGROUND OF THE INVENTION

The invention relates to measuring tracheotomy stomas for proper fitting of a tracheal cannula.

A tracheotomy tube or cannula, e.g., like that shown in Montgomery U.S. Pat. No. 4,269,184, is used to provide access to the trachea. Tracheotomy tubes typically are made of plastic and include a cylindrical portion within the tracheotomy stoma, which is surgically provided prior to insertion of the tube.

SUMMARY OF THE INVENTION

In general, the invention features a tool used to accurately measure a patient's tracheotomy stoma for precise fitting of a tracheotomy tube.

In one aspect, the tool has a plurality of legs that are integrally connected to each other and are sufficiently long to extend from the outside of a patient's skin to inside the tracheal passage and are spaced from other legs by at least 90° or more so as to not interfere when inserting other legs into the tracheotomy stoma. Each leg is generally cylindrical over most of its length and has a diameter that corresponds to one of a plurality of different tracheotomy tube diameters.

In preferred embodiments, there are three legs that are at 90° angles to each other; one leg is about 10 mm in diameter; one leg is about 8 mm in diameter; and one leg is about 6 mm in diameter. The legs are between 30 mm and 60 mm in length.

In another aspect, the tool has a shaft portion with a bent end for engaging the inside surface of the patient's tracheal passage and length indicia along its length indicating the distance to the bent end. A ring member is sized and shaped to releasably engage the shaft at various positions along the shaft so as to indicate a particular length indicia when pushed up against the patient's skin when the bent end engages the inside surface of the tracheal passage.

In preferred embodiments, the shaft includes small circumferential protuberances that releasably engage the ring at calibrated positions. The bent end is bent at about a 135° angle to provide a gentle bend that is easy to insert through the tracheotomy stoma. The tube is made of medical grade silicone materials.

With the accurate measurements of stoma diameter and length permitted by the tool, the surgeon can select a custom-fit tracheal tube to provide optimum results.

Other advantages and features of the invention will be apparent from the following description of a preferred embodiment and from the claims.

DESCRIPTION OF THE PREFERRED EMBODIMENT

The preferred embodiment will now be described.

DRAWINGS

STRUCTURE

Figure 1:
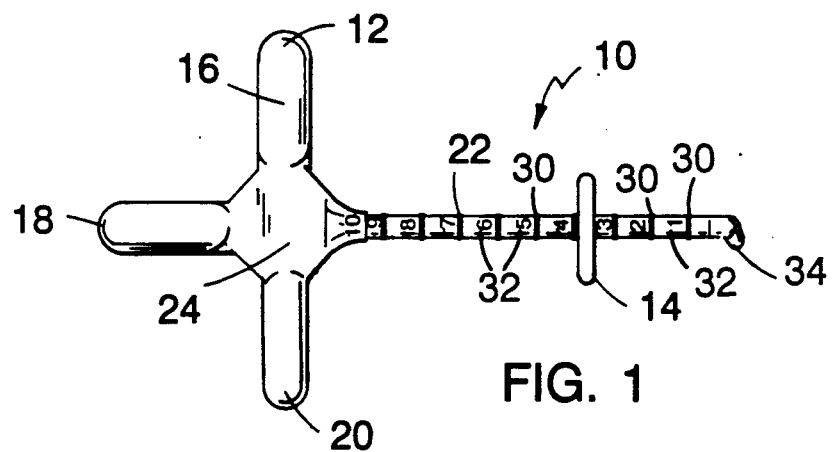
FIG. 1 is a plan view of a tool for measuring a tracheotomy stoma according to the invention.

Referring to FIG. 1, tracheotomy tool 10 includes integral member 12 and ring 14. Integral member 12 has three legs 16, 18, 20 and calibrated shaft 22, all of which extend outward from hub 24 along axes making 90° angles with each other in a plane. Leg 16 has a 10 mm diameter; leg 18 has an 8 mm diameter; and leg 20 has a 6 mm diameter. Legs 16, 18, 20 are each about 35 mm long, which permits the legs to be inserted all the way through a stoma from the patient's skin 26 to the inner surface 28 of the tracheal passage. Calibrated shaft 22 has circumferential protuberances 30 spaced at 1 cm distances along its length and half-cm markers 32 between protuberances 30. Numerical indicia "1" to "10" are also included adjacent to respective protuberances 30. Integral member 12 and ring 14 are made of medical grade silicone material which is flexible and deformable.

Figure 2:
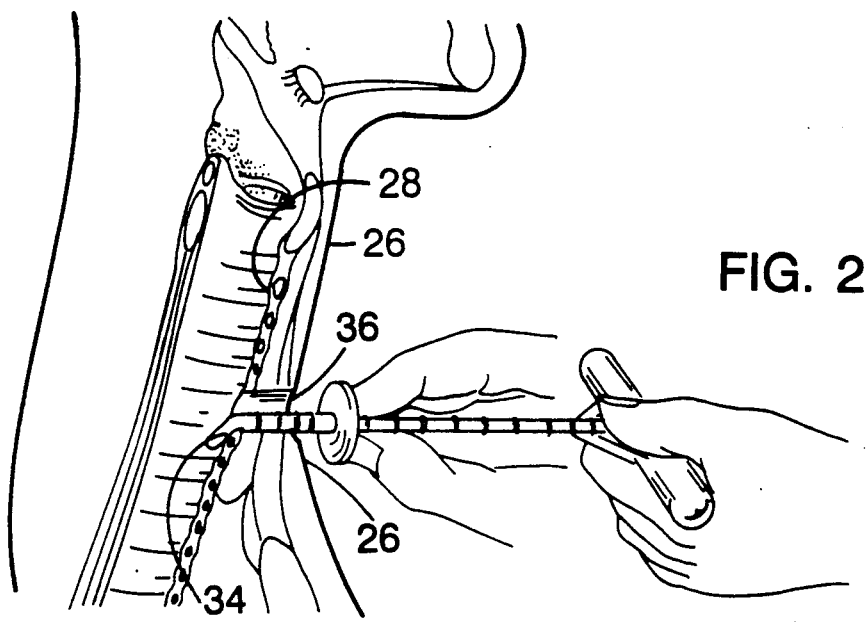
FIG. 2 is a diagrammatic, partially sectional view showing use of the FIG. 1 tool to measure the length of a tracheotomy stoma in a patient.
Figure 3:
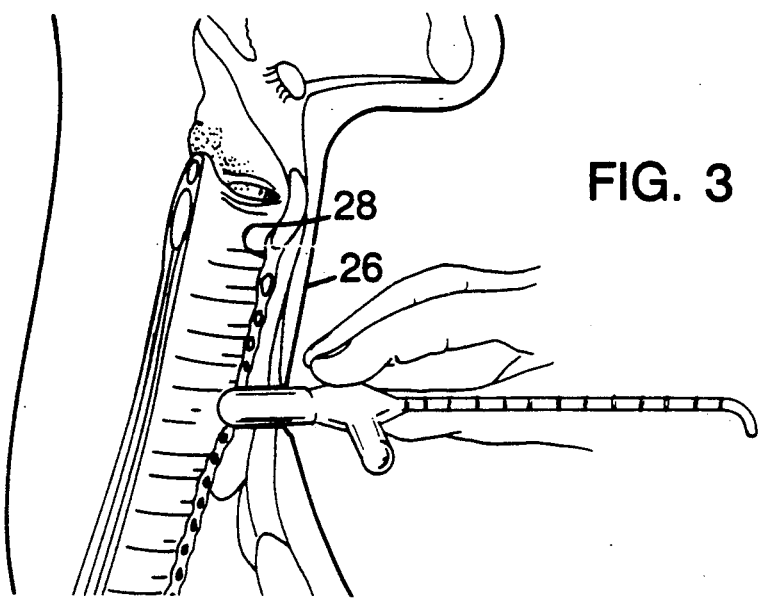
FIG. 3 is diagrammatic partially sectional view showing use of the FIG. 1 tool to measure the diameter of a the tracheotomy stoma.

The inner diameter of ring 14 is slightly less than the outer diameter of protuberances 30 and slightly greater than the outer diameter of shaft 22 between protuberances 30 in order to releasably engage shaft 22 along its length. Shaft 22 has a bent end 34, shown best in FIG. 2. It is bent at an axis making a 135° angle with the rest of shaft 22.

USE

In use, the surgeon prepares tracheotomy stoma 36 at the desired location, inserts bent end 34 through the stoma, places the shaft against the side of the stoma, and gently pulls the shaft out until bent end 34 engages inner surface 28. Ring 14 is then pushed up against the surface 26 of the patient's skin, and tool 10 can then be removed with location ring 14 indicating the length of the stoma. The surgeon then tries inserting legs 16 through 20, starting with the smallest diameter leg 20 first and then trying legs 16, 18 to determine the diameter of stoma 26. With these accurate length and diameter measurements, the surgeon can then select from an assortment of different tracheotomy tubes to obtain one that is custom fit. Legs 16-20 desirably perform the dual function of a handle used when making length measurements and the means for making the diameter measurements. Device 10 is sterilizable by autoclaving and can thus be reused.

Other embodiments of the invention are within the scope of the appended claims.

What is claimed is:

1. A tracheotomy stoma measuring gauge for measuring a tracheotomy stoma for proper fitting of a tracheotomy tube having a circular section and an outer diameter comprising an integral member having three legs that extend from it, each said leg having a free end and a base end secured to other legs, each said leg being sufficiently long to extend from the outside of a patient's skin to inside the patient's tracheal passage, each said leg being spaced from other legs by at least about 90° or more so as to not interfere with insertion into said tracheotomy stoma, each said leg having a length between 30 mm and 60 mm, said legs having blunt ends, each said leg being generally cylindrical over most of its length and having a diameter that corresponds to said tracheotomy tube outer diameter and is different than the diameters of other legs, said legs having diameters between 6 mm and 12 mm.

2. The tool of claim 1 wherein said legs are spaced from each other by about 90° angles in the same plane.

3. The tool of claim 2 wherein there are three said legs, and they are about 6 mm, about 8 mm and about 10 mm in diameter.

4. The tool of claim 1 wherein said tool is made of silicone material.

5. A tracheotomy stoma measuring gauge for measuring a tracheotomy stoma for proper fitting of a tracheotomy tube comprising an integral member having a shaft portion, said shaft portion having a straight portion and a single bent end for engaging the inside surface of a tracheal passage, said straight portion and said bent end having substantially the same diameter, said straight portion and said bent end meeting at a point and forming an angle with each other, said straight portion and said bent end being integral and fixed with respect to each other, said straight portion of said shaft having length indicia along its length indicating the distance to the bent end, and a ring having means to releasably engage said shaft at various positions along said shaft so as to indicate a particular said length indicia when pushed up against the patient's skin when said bent end engages the inside surface of said tracheal passage.

6. The tool of claim 5 wherein the shaft has circumferential protuberances along its length to engage said ring.

7. The tool of claim 6 wherein said shaft is less than about 5 mm in diameter.

8. The tool of claim 7 wherein said bent end is bent at about a 135° angle with said shaft.

9. A tracheotomy stoma measuring gauge for measuring a tracheotomy stoma for proper fitting of a tracheotomy tube having a circular section and an outer diameter comprising an integral member having a plurality of legs that extend from it, each said leg having a free end and a base end secured to other legs, each said leg being sufficiently long to extend from the outside of a patient's skin to inside the patient's tracheal passage, each said leg being spaced from other legs by at least about 90° or more so as to not interfere with insertion into said tracheotomy stoma, each said leg having a length, each said leg being generally cylindrical over most of its length and having a diameter that corresponds to said tracheotomy tube outer diameter and is different than the diameters of other legs, said integral member also having a shaft portion, said shaft portion having a bent end for engaging the inside surface of the tracheal passage, said shaft having length indicia along its length indicating the distance to the bent end, and a ring having means to releasably engage said shaft at various positions along said shaft, so as to indicate a particular said length indicia when pushed up against the patient's skin when said bent end engages the inside surface of a tracheal passage.

10. The tool of claim 9 wherein said legs are spaced from each other by about 90° angles in the same plane and are between about 6 mm and 12 mm in diameter.

11. The tool of claim 10 wherein there are three said legs, and they are about 6 mm, about 8 mm and about 10 mm in diameter.

12. The tool of claim 11 wherein said legs are between 30 mm and 60 mm long.

13. The tool of claim 12 wherein the shaft has circumferential protuberances along its length to engage said ring.

14. The tool of claim 13 wherein said shaft is less than about 5 mm in diameter.

15. The tool of claim 14 wherein said bent end is bent at about a 135° angle with said shaft.

16. The tool of claim 9 wherein said tool is made of silicone material.

* * * * *